United States Patent [19]

Zumbrunn

[11] 4,230,478

[45] Oct. 28, 1980

[54] DEODORANT COMPOSITION FOR ANIMAL AND VEGETAL WASTES

[75] Inventor: Jean-Pierre Zumbrunn, Eaubonne, France

[73] Assignee: L'Air Liquide S.A. pour l'Etude et l'Exploitation des Procedes George Claude, Paris, France

[21] Appl. No.: 5,836

[22] Filed: Jan. 23, 1979

[30] Foreign Application Priority Data

Feb. 3, 1978 [FR] France .................... 78 03000

[51] Int. Cl.$^3$ .......................................... C05F 3/00
[52] U.S. Cl. ................................................ 71/3; 71/4; 71/21; 252/174.11; 252/95; 210/759
[58] Field of Search .............. 71/21, 13, 22, 11, 23, 71/14, 25, 12, 26, 64 R, 64 JC, 3, 4; 210/63 R, 64; 252/95, 49.5, 174.11, 174.21

[56] References Cited

U.S. PATENT DOCUMENTS

| 975,405 | 11/1910 | Eilertsen | 210/63 R |
|---|---|---|---|
| 1,509,062 | 9/1924 | Hoover | 71/14 X |
| 2,558,942 | 7/1951 | Eagleson | 71/21 X |
| 3,507,798 | 4/1970 | Egan et al. | 252/174.21 X |
| 3,705,098 | 12/1972 | Sheperd et al. | 210/63 R |
| 3,785,971 | 1/1974 | Halley et al. | 210/64 |
| 3,883,303 | 5/1975 | Roberts | 210/64 X |
| 3,966,450 | 6/1976 | O'Neill et al. | 210/63 R X |
| 4,160,656 | 7/1979 | Junkermann | 71/21 |

FOREIGN PATENT DOCUMENTS

| 2026735 | 12/1971 | Fed. Rep. of Germany | 71/3 |
|---|---|---|---|
| 2047638 | 3/1972 | Fed. Rep. of Germany | 71/21 |
| 2310135 | 5/1975 | France . | |

*Primary Examiner*—Kenneth M. Schor
*Attorney, Agent, or Firm*—Browdy and Neimark

[57] ABSTRACT

A deodorant composition is made up of an oxygen carrying element associated with a synergistic odor-masking compound, and a biodegradable emulsifying surfactant. It can be used in the form of an emulsion or of the two separate constituents, and applicable to deodorizing organic or vegetal wastes and byproducts which normally release nauseating or harmful odors essentially made up of nitrogen or sulfur derivatives.

7 Claims, No Drawings

DEODORANT COMPOSITION FOR ANIMAL AND VEGETAL WASTES

FIELD OF INVENTION

This invention relates to a composition for deodorizing organic or vegetal byproducts which release nauseating odors made up essentially of nitrogen or sulfur derivatives.

BACKGROUND OF INVENTION

Organic byproducts, particularly animal wastes such as manure, are used as fertilizer in meadows and cultivable lands on which they are spread. However, their disagreeable odor, which may be even harmful when hydrogen sulfide is released, makes storage and spreading of these manures extremely polluting for the neighboring areas. Many efforts have been made to combat the bad odors of these byproducts, particularly of animal origin, such as manure from farm animals or intensive stockraising.

W. H. Kibbel et al proposed a process of treating animal wastes with hydrogen peroxide (27th Industrial Waste Conference, Purdue University, May 2–4, 1972). U.S. Pat. No. 3,966,450 relates to the use of hydrogen peroxide in the presence of phosphoric, sulfuric or nitric acids alone or in mixture. However, it should be noted that hydrogen-peroxide-phosphoric acid solutions are not stable in useful concentrations, the strength droping rapidly, and the loss can reach 30% in a month. Specially stabilized hydrogen peroxide does not seem to give the expected solution, particularly because of its high cost.

French Pat. No. 2,310,135 proposed, for deodorizing manures, a liquid composition with a high content of terpene product, from 85 to 97% by weight, to which is added 3 to 15% by weight of an emulsifying agent.

SUMMARY OF INVENTION

According to the invention a deodorizing composition has now been found, which is simple and fast to use and which inhibits the odors from wastes during storage and handling and for a sufficiently long time during spreading and until assimilation by the soil. The period of inhibition of the odor is sufficient to proceed to spreading of the manure or other wastes without disagreeable odor in the immediate vicinity. The deodorizing action lasts so long that the constitutents of the manure are assimilated by the soil before the odor can reappear.

This composition is made up of an oxygen releasing component such as hydrogen peroxide, associated with a component having a synergistic action for masking the nauseating odors, such as a terpene aromatic compound or a mixture of terpenes, and a biodegradable nonionic emulsifying surfactant, for example, of the polyoxyethylene type.

DETAILED DESCRIPTION OF EMBODIMENTS

The hydrogen peroxide reacts on hydrogen sulfide and the nitrogen and sulfur organic materials of the manure. The oxygen of the hydrogen peroxide is transferred by chemical action to these very smelly products, oxidizing them so that their nauseating odor is destroyed or almost completely attenuated. For example, very odorous and toxic hydrogen sulfide is transformed into sulfates or colloidal sulfur by one or other of the following reactions:

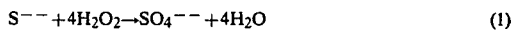

$$S^{--} + 4H_2O_2 \rightarrow SO_4^{--} + 4H_2O \quad (1)$$

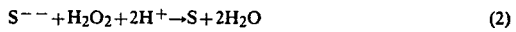

$$S^{--} + H_2O_2 + 2H^+ \rightarrow S + 2H_2O \quad (2)$$

One or other of these reactions will be initiated depending on the pH of the material to be deodorized. Reaction (1) occurs with a pH equal to or greater than 8.5–9 and reaction (2) at more acidic pH. Some animal manures have a pH close to 7; thus reaction scheme 2 will occur. The colloidal sulfur formed is inert and does not chemically react with other products to give foul smelling sulfur products.

The synergistic compound is advantageously an aromatic compound selected from the group of terpene derivatives; more especially pine terpene derivatives alone or in mixture, such as pine oil, the sesquiterpenes of turpentine, have been selected for their effective and lasting action.

Aromatic essence and particularly pine oil acts according to an identifiable phonomenon to provide a masking effect. Its odor is superposed on that of nauseating product so that it is preferentially smelled by making undetectable those odors it is not desired to smell.

It has been found however, that each of the base constituents of the present formulation, taken separately, have only a moderate effect on the suppression of disagreeable odors, but that the sum of both, by a synergistic effect, gives a markedly better result. Even in slight doses the mixture gives excellent results, whereas each one taken separately must be used in massive doses to obtain a detectable result, without really giving satisfactory results.

For example, to deodorize hog manure under good conditions, with hydrogen peroxide alone, it was observed in testing that it was necessary to obtain satisfactory results, to mix at least 2 liters of a 35% solution per m³ of manure. To mask in a sufficiently perceptible manner the odor of manure with pine oil or turpentine sesquiterpenes, it was observed that it was necessary to incorporate at least 0.5 liter per m³ of manure whereas with the 35% hydrogen peroxide + terpene derivative mixture, doses of 0.5 liter of the first product +0.2 liter of the second, per m³ of manure, achieved a superior result.

Hydrogen peroxide is soluble in any portions in water and preponderantly aqueous liquids, but pine terpene derivatives are insoluble.

If incorporation in the product to be deodorized is performed without special precautions, the essences have a tendency to salt out in the treated waste and, considering their density which is close to 0.9, they will lie mostly on the surface, making the treatment of the lower layers haphazard.

It has been established that the incorporation of an emulsifying agent, perferably of the polyoxyethylene non-ionic class, makes it possible to disperse the aromatic agent in the aqueous medium, thus making possible homogeneous treatment of the entire mass to be deodorized. This type of emulsifier by its biodegradable character corresponds well to the desired effect: deodorizing of a fertilizing product, without causing secondary pollution due to the products used. In case biodegradability of the surfactant is not essential or desired, an anionic type emulsifier can be used without other drawbacks.

It has also been found that the dispersing agent has another and unexpected effect, i.e. it makes it possible to obtain a stable emulsion of the diluted hydrogen peroxide used as the deodorizing coproduct and then with the manure. It is possible to prepare a stable and inoffensive deodorizing composition for the natural medium, made up of dilute hydrogen peroxide and pine terpene derivatives, pine oil for example, with the dispersant or emulsifier.

By laboratory tests, it was established that the emulsion should have the following composition (it being understood that equivalent materials may be substituted for those preferred ingredients specified):

Hydrogen peroxide expressed in 100% $H_2O_2$:50 to 500 g/l, preferably 200 g/l.
Pine oil: 50 to 400 ml, preferably 200 ml.
Polyoxyethylene type nonionic emulsifier: 5 to 50 g/l, preferably 20 g/l.
Sufficient water to make 1 liter of emulsion. The mixture thus made up has the appearance of a white milk.

In certain cases, it was found that after a long storage of the emulsion, before use, a separation of the oxygenated aqueous and terpene constitutents occurred. A moderate agitation or a mixing of the liquids generally makes it possible to reconstitute the milky emulsion ready for use.

But it was also observed that with use of pine terpene derivatives alone or in mixture, with a boiling point higher than pine oil, such as heavy fractions of turpentine whose masking action is similar, the emulsion is more difficult to reconstitute. In this particular case of use of these aromatic fractions, it has been found that the constitutents can be stored separately to be mixed at the time of use or again be introduced successively in the mixture to be deodorized. The mode of operation hs no adverse effect on the final result.

According to a variant of the invention, the emulsion is replaced by two separate constituents. The first is an aqueous solution of hydrogen peroxide whose concentration can be in any amount, but advantageously it is close to 30 to 50%, i.e., containing 330 to 600 g/liter of 100% $H_2O_2$. The second is a pine terpene derivative made self-emulsifying by incorporation of 1 to 10%, preferably 5%, i.e., 10 to 100 g/l, preferably 50 g/liter of solution, of a surfactant similar to that used for the emulsified mixture.

For treatment of normally fermented hog, calf, poultry manure, there are used 0.1 to 1 liter of oxidant carrying element and 0.1 to 1 liter of self-emulsifying masking agent, stored separately and mixed at the time of use, per $m^3$ of manure. Excellent results are obtained by deodorizing with 0.3 to 0.5 liter of oxidant carrying element and 0.3 to 0.5 liter of self-emulsifying masking agent under the same conditions as above.

Incorporation of the composition achieves a deodorizing effect on all types of vegetal and animal wastes, particularly:

manure of farm and stockraising animals, such as hogs, cattle and poultry,
vegetable wastes: sugar beet musts, residuary liquor, etc.

Use of the deodorizing emulsion, for example for animal manures, is accomplished by incorporation into the manure mass stored in a tank or directly in a manure barrel, a device currently used for spreading. The emulsion is introduced and mixed in the desired proportions by using either equipment designed for this use and known as automatic additive dosers, or by mixing the product in the manure ditch, or by introducing the deodorizing charge in the manure suction pipe of which one end goes into the tank and the other end is later connected to the barrel. In all cases, the presence of the emulsifying agent makes possible the simple and easy dispersion of the deodorizer to obtain a homogeneous mixture.

Use of the variant of the invention is similar to that of the emulsified mixture except that there are incorporated successively, but under the same conditions, the oxygen carrying solution and the self-emulsifying terpene masking agent. Incorporation in the product to be deodorized can be performed in any order, the results being identical.

It was found, during testing on the soil, that the effect of the mixture continues long enough for no disagreeable odor to be observed after spreading, during the time necessary for assimilation of the product spread on the ground, namely several days.

Examples that illustrate the invention is a non-limiting way are given below.

EXAMPLE I

One liter of a deodorizing emulsion is prepared by mixing, with agitation, 500 ml of 35% hydrogen peroxide, 200 ml pine oil, 15 ml of polyoxyethylene nonionic surfactant and 285 ml of water.

EXAMPLE II

Into a tank of 50 $m^3$ containing 40 $m^3$ of hog manure, supplied for several weeks, are added 30 liters of the emulsion described in example I. The effect is immediate from the time of homogenization of the mixture which is spread without delay by standard means. No odor is detectable in the immediate vicinity either at the time of spreading or later during the assimilation period.

EXAMPLE III

The feed pipe of a hog or calf manure barrel, immersed at one of its ends in a manure ditch, is provided on the other end with 3 liters of the deodorizing emulsion described in example I. The pipe is then connected to the manure barrel, having a capacity of 4 $m^3$, which is then put under low pressure by the pump incorporated in the equipment. The emulsion is aspirated with the manure and mixed. The filled barrel is then carried to the spreading field and the mixture is spread. The same results as those described in example II are obtained.

EXAMPLE IV

The deodorizing emulsion of example I is used under the same conditions as those of example III but it is introduced into the barrel by an automatic incorporation device. The same results as those described in examples II and III are obtained.

EXAMPLE V

One liter of self-emulsifying masking aromatic agent is prepared by mixing 950 ml of a terpene derivative—distillation fraction of turpentine—made up mainly of sesquiterpenes, with 50 ml of polyoxyethylene nonionic surfactant.

EXAMPLE VI

Into a tank of 50 $m^3$, containing 40 $m^3$ of hog or calf manure, supplied for several weeks, are added 10 liters of the self-emulsifying aromatic agent described in example V and 20 liters of 50% hydrogen peroxide solution. The results are identical with those described in example II.

EXAMPLE VII

Following the procedure of example III, one end of a feed pipe of a hog or calf manure barrel is immersed in manure and through the other end there are introduced 1 liter of the self-emulsifying aromatic agent according to example V then 2 liters of 50% hydrogen peroxide solution. The performance of the operations is then carried out identical with that described in example III. The results are the same.

EXAMPLE VIII

Also according to the procedure of example III, one end of a feed pipe of a calf manure barrel with a capacity of 4 m$^3$ is immersed in manure. Through the other end, there are introduced 1.6 liters of self-emulsifying agent according to example V then 1.6 liter of 35% hydrogen peroxide solution. The performance of the operations is identical with that described in example III. The self-emulsion of the two deodorizing constituents with the manure is effected by itself during the aspiration of the mixture to the manure barrel. The same results as those described in example II are obtained.

EXAMPLE IX

The operation is under the same conditions as in the previous example but by treating hog manure and reversing the order of introduction of the reagents used at a rate of 1.2 liter of 35% hydrogen peroxide solution and then 1.2 liters of self-emulsifying aromatic agent according to example V. The results are the same as those previously obtained.

EXAMPLE X

Poultry manure made more fluid by diluting with water is deodorized by operating according to the conditions of example VIII. The results obtained are similar to those of example II.

It will be obvious to those skilled in the art that various changes may be made without departing from the scope of the invention and the invention is not to be considered limited to what is described in the specification.

What is claimed is:

1. A deodorizing composition consisting essentially of an aqueous mixture of an oxygen generating compound, an odor masking agent, and an emulsifying effective amount of a biodegradable emulsifying surfactant, wherein the oxygen generating compound is hydrogen peroxide at a concentration expressed at 100% $H_2O_2$ of 50 to 500 g/liter of said aqueous mixture, the odor masking agent is a pine oil or the sesquiterpenes of turpentine, present in a concentration of 50 to 400 ml/l of said aqueous mixture, and the emulsifying surfactant concentration is 5 to 50 g/l of said aqueous mixture.

2. Deodorizing composition according to claim 1 wherein the masking agent is a terpene aromatic compound or mixture of terpenes, and said surfactant is of the polyoxyethylene type.

3. A deodorizing composition consisting essentially of an aqueous mixture of an oxygen generating compound, an odor masking agent, and an emulsifying effective amount of a biodegradable emulsifying surfactant, wherein the oxygen generating compound and masking agent are mixed at the time of use, the oxygen generating compound being hydrogen peroxide solution in a concentration between 30 and 50% hydrogen peroxide corresponding to 330 to 600 g/liter of 100% $H_2O_2$, and the masking agent being a pine oil or the sesquiterpenes of turpentine made self emulsifying by incorporation of a polyoxyethylene type surfactant introduced in an amount of 1 to 10% surfactant per liter of masking agent said surfactant constituting from 10 to 100 g/liter.

4. A composition according to claim 3 wherein said surfactant is introduced at a rate of about 5% per liter of masking agent constituting about 50 g/l of solution.

5. A process for the treatment of normally fermenting animal wastes, including hog, calf or poultry manure, to inhibit the odors normally emanating therefrom, comprising mixing with said fermented waste from 0.1 to 1 liter of hydrogen peroxide solution in a concentration between 30 and 50% hydrogen peroxide corresponding to 330 to 600 g/liter of 100% $H_2O_2$ and 0.1 to 1 liter of a masking agent which is pine oil or sesquiterpenes of turpentine made self emulsifying by incorporation of a polyoxyethylene type surfactant introduced in an amount of 1 to 10% surfactant per liter of masking agent said surfactant constituting from 10 to 100 g/liter.

6. A process according to claim 5, wherein said hydrogen peroxide solution and said masking agent are mixed immediately prior to mixing with said fermented waste.

7. Process of treatment of normally fermented wastes in accordance with claim 5, whereby there are used 0.3 to 0.5 liters of said oxygen generating compound and 0.3 to 0.5 liters of said self-emulsifying masking agent per m$^3$ of manure.

* * * * *